United States Patent [19]
Reddy et al.

[11] Patent Number: 5,085,743
[45] Date of Patent: Feb. 4, 1992

[54] ELECTRODE FOR CURRENT-LIMITED CELL, CELL INCLUDING THE ELECTRODE METHOD FOR USING THE CELL AND A METHOD OF MAKING THE ELECTRODE

[75] Inventors: N. R. K. Vilambi Reddy, Salem, N.H.; Everett B. Anderson, Reading; Earl J. Taylor, Chelmsford, both of Mass.

[73] Assignee: Physical Sciences, Inc., Andover, Mass.

[21] Appl. No.: 518,071

[22] Filed: May 2, 1990

[51] Int. Cl.$^5$ .................................................. C25D 5/18
[52] U.S. Cl. ........................... 205/105; 204/153.16; 204/431; 204/432; 429/40; 429/42; 205/161; 205/196
[58] Field of Search ............... 204/38.5, 38.7, 153, 204/161, 431, 432; 429/40, 41, 44

[56] References Cited

U.S. PATENT DOCUMENTS

| | | | |
|---|---|---|---|
| 3,196,050 | 7/1965 | Thompson | 204/294 |
| 3,239,382 | 3/1966 | Thompson | 136/86 |
| 3,252,839 | 5/1966 | Langer et al. | 136/86 |
| 3,276,976 | 10/1966 | Juliard | 204/290 |
| 3,287,168 | 11/1966 | Marsh | 136/86 |
| 3,322,576 | 5/1967 | Young | 136/121 |
| 3,340,097 | 9/1967 | Hess et al. | 136/120 |
| 3,446,607 | 5/1969 | Volk et al. | 29/195 |
| 3,461,044 | 8/1969 | Lyons et al. | 204/3 |
| 3,471,338 | 10/1969 | Trachtenberg | 136/120 |
| 3,600,227 | 8/1971 | Hardman | 136/76 |
| 3,663,303 | 5/1972 | Dietz | 136/122 |
| 3,715,238 | 2/1973 | Mayell | 136/120 |
| 3,796,607 | 3/1974 | Schaer et al. | 136/19 |
| 3,802,922 | 4/1974 | Meibuhr | 136/120 FC |
| 3,899,351 | 8/1975 | Maurer et al. | 136/34 |
| 4,042,464 | 8/1977 | Blurton et al. | 204/1 T |
| 4,132,606 | 1/1979 | Crespy et al. | 204/2.1 |
| 4,141,301 | 2/1979 | Perry | 204/2.1 |
| 4,242,179 | 12/1980 | Fritts et al. | 204/2.1 |
| 4,265,714 | 5/1981 | Nolan et al. | 204/1 T |
| 4,273,839 | 6/1981 | Carr et al. | 429/51 |
| 4,425,192 | 1/1984 | Mckinley | 204/2.1 |
| 4,454,649 | 6/1984 | Jalan et al. | 29/623.5 |
| 4,729,824 | 3/1988 | Giner | 204/415 |
| 4,820,386 | 4/1989 | LaConti et al. | 204/1 T |

FOREIGN PATENT DOCUMENTS

0011071 5/1980 European Pat. Off. .

OTHER PUBLICATIONS

Miwa, K. et al., "Electrode Substrate for Phosphoric Acid Fuel Cell" (trade lit. of Toray Ind. Inc., Shiga, Japan), 4 pages.

*Primary Examiner*—John Niebling
*Assistant Examiner*—Kathryn Gorgos

[57] ABSTRACT

The gas-sensing electrodes prepared according to this invention are specifically designed for cells which operate in a current-limited mode, i.e. at current densities well below 20 mA/cm$^2$. Such cells are particularly useful to measure or detect a gaseous component of a gaseous environment or stream, provided the gaseous component can be electrochemically oxidized or reduced. In an alkaline, metal-oxygen cell for example, an electrode of this invention can be used as an oxygen cathode. The electrode is prepared by:

(a) bringing an exposed face of a self-supporting, electrically-conducting sheet of fibrous or sintered-particle material having a thickness of at least about 30 $\mu$m and a flexural strength of at least 2000 kPa into contact with an electrolyte containing ions of a catalytic metal, the electrolyte also being in contact with a counterelectrode, (b) applying a pulsed-D.C. current which tends to favor electroplating of metal and strong adherence of the plated metal to the electrically-conducting sheet, so that a continuous electrodeposited layer of catalytic metal is formed, and (c) applying a hydrophobic layer to the thus-plated face, this hydrophobic layer being thick enough to limit gas diffusion into the cross-section of the sheet, so that the resulting electrode will operate in a current-limited mode, but not so thick as to have a significant adverse effect upon the response time of the cell.

18 Claims, No Drawings

ELECTRODE FOR CURRENT-LIMITED CELL, CELL INCLUDING THE ELECTRODE METHOD FOR USING THE CELL AND A METHOD OF MAKING THE ELECTRODE

Work related to this invention was supported by a grant from the National Science Foundation.

Technical Field

This invention relates to electrodes designed for cells which operate at low current densities, i.e. less than about 20 milliamperes per square centimeter of electrode surface (20 mA/cm$^2$), more typically less than about 10 mA/cm$^2$, e.g. for cells used as gas sensors. An aspect of this invention relates to gas sensor electrodes with fast response time capabilities and sufficient structural strength to be self-supporting. Another aspect of this invention relates to electrodes and cells which are simple and inexpensive to produce and have long-term stability when in use. Still another aspect of this invention relates to a method for preparing a gas sensor electrode utilizing the pulsed electro-deposition technique.

Description of the Prior Art

Most electricity-producing and electrolytic cells are designed for relatively high current operation, e.g. above 50 mA/cm$^2$, more typically above 100 mA/cm$^2$. High current operation is particularly desirable for fuel cells, metal/air or metal/oxygen cells, electrolysis cells, and the like. Thus, it would ordinarily be very undesirable for an air cathode or oxygen cathode designed for any of these types of cells to be limited to low current density operation, e.g. currents less than 20 mA/cm$^2$.

An entirely different set of operating parameters is normally contemplated for cells designed for chemical analysis or detection, e.g. for analyzing (measuring or detecting or sampling) substances in an environment or fluid stream or the like. Electrochemical cells with measurement or detection or chemical analysis capabilities do not require large currents, because the principal design objective for these cells is to relate changes in either voltage or current to the presence or amount of substance to be detected or measured. (These changes in current flow or voltage may be very small.) Lifetime stability of potential is a particularly desirable feature of these detection or analysis cells.

The principles described above are well illustrated by the art of making gas-sensor cells. In a gas-sensor cell, a flow of gas containing some component to be detected or measured is passed over an electrode, most preferably a metallic electrode, e.g. a metal-plated film or foraminous sheet. The component of the gas stream which is to be analyzed for should be capable of being oxidized or reduced on the surface of the electrode. For example, oxygen, oxides of carbon such as carbon dioxide, oxides of sulfur, oxides of nitrogen, gaseous halogens, and the like are reducible and can be detected at the cathode of a gas-sensing cell. Hydrogen, oxidizable organic compounds, sulfur dioxide, carbon monoxide, oxidizable mercaptans, etc. can be detected at a suitably designed anode. Some noxious gases (e.g. hydrogen sulfide) can be either oxidized or reduced; hence, many design options are available for cells made to detect or measure this gas.

One particularly important use of gas-sensing cells lies in the field of oxygen analysis. There are various situations in which it is important to be able to measure the oxygen content of a gas stream, e.g. a stream of air or anesthesia gas or the oxygen supply for a patient under anesthesia. During a surgical procedure in which the patient is under anesthesia and is receiving a carefully preselected mixture of gases for respiration, it is important to know the oxygen content of this mixture, preferably on a breath-by-breath basis, which would require cell response times on the order of a few seconds or less. It is known in the oxygen-sensing art to insert an electrochemical cell having an oxygen cathode in the gas stream flowing to the patient. These cells are designed to operate under "current limited" conditions, e.g. current densities on the order of 10 mA/cm$^2$ or less. The cell may, if desired, have a small current or a constant potential imposed upon it, but more typically, the cell is like a small metal/oxygen cell capable of generating a current through oxidation of a metal anode and reduction of oxygen at the cathode. Ideally, the current generated by the reduction of oxygen to water or hydroxide or peroxide will be correlatable precisely with the oxygen content in the gas stream. Some of these oxygen-sensor cells are alkaline (i.e., they have alkaline electrolytes). These alkaline cells can have a very simple and inexpensive anode comprising, for example, a metal which is consumed (oxidized to alkali-soluble metal ions) during the electrochemical reaction or, less preferably, a metal which is relatively inert or which forms alkali-insoluble oxides or hydroxides when electrochemically oxidized. The selection of the electrocatalytic metal for the oxygen cathode requires considerably more thought. Many metals are too reactive with alkaline electrolytes on the cathode side of the cell. Gold and gold alloys and platinum are known to be well suited for use in oxygen cathodes of alkaline cells. However, special problems are encountered when gold-containing cathodes are prepared specifically for this purpose.

Existing gold cathodes for oxygen-sensing cells tend to have various disadvantages. These cathodes may be in the form of gold particles or layers deposited on a hydrophobic polymer film, in which case the resulting cathode is too flimsy to lend itself to mass-production techniques, and each gold cathode must be laboriously inserted in the cell structure. Another drawback is that these gold cathodes may have to be relatively high in gold content; for example, each geometric square centimeter of cathode surface may have to contain at least 15 or 20 milligrams of gold—as compared to the 0.5 to 5 mg/cm$^2$ loadings typical of the state of the art of fuel cell type electrodes (e.g. gold-on-carbon or platinum-on-carbon electrodes). The thickness of the hydrophobic polymer film cannot be significantly increased to provide more rigidity, because the time it takes to diffuse through this film is very important, at least in medical and surgical applications of this technology. For example, a 30-second response time for the oxygen measurement would be detrimental to breath-by-breath monitoring of the oxygen supply to a patient. (Indeed, the ideal response time is less than about a second, most preferably in the hundreds of milliseconds.)

It is known in the art of gas-diffusion electrodes (GDE's) that very economical use of expensive catalytic metals such as gold or the Group VIII noble metals can be obtained by "supporting" these metals with a relatively inexpensive current-conducting, particulate material such as carbon. It is has been suggested that supported gold is a particularly good electrocatalytic material for gas-sensing electrodes. See, for example, U.S. Pat. No. 4,042,464 (Blurton et al), issued Aug. 16, 1977. For additional background in the art of gas-sensing electrodes, see U.S. Pat. No. 4,265,714 (Nolan et al), issued May 5, 1981. Other support materials have been suggested for GDE-type electrodes generally, including special forms of carbon in which the carbon is in the form of fibers. A wide variety of techniques has been used to deposit gold and/or Group VIII noble metals on support materials, including in-situ reduction with chemical reducing agents, electrochemical reduction of metal compounds such as chlorauric acid, gold (III) chloride, gold cyanide, gold dissolved in aqua regia (as gold salts), etc. According to the Blurton et al patent cited above, for example, absorbent carbon may be impregnated with a solution of a gold salt decomposable to gold oxide, heating the impregnated carbon to a temperature at which this decomposition will take place, and then reducing the gold oxide in the presence of hydrogen to the catalytically active free metal. The gold salt or salts can be prepared in solution form by dissolving gold metal in aqua regia.

SUMMARY OF THE INVENTION

It has now been found that a gas sensing electrode especially well suited to current limited operation (e.g. operation at current densities below about 10 mA/cm$^2$ and in virtually all cases below 20 ma/cm$^2$), which is physically rigid, but which can have a very fast response time is attainable and can be made with gold loadings comparable to those of state-of-the-art supported gold electrodes, e.g. loadings of 0.1 to 5 mg/cm$^2$. The physical rigidity of the electrodes of this invention is believed to be ideal for automated electrode preparation and gas-sensor cell assembly. Response times of less than 5 seconds (more typically <1 second) can be provided by selecting a thickness for the hydrophobic polymer layer on the "gas" side of the electrode which is thin enough to permit rapid diffusion of gas into the electrode structure but still thick enough to ensure current-limited operation. Gas diffusion electrodes of this invention have a flexural strength of at least 2000 kilopascals (kPa), e.g. 15,000 kPa or more (>2000 psi). These electrodes are made by:

(a) bringing an exposed face (which is to become the "catalyst side" or "catalyst face") of a self-supporting, electrically-conducting porous sheet (preferably comprising carbon fibers) having a thickness of at least about 30 micrometers (um) and a flexural strength of at least 2000 kPa into contact with an electrolyte containing ions of a catalytic metal, the electrolyte also being in electrical contact with a counterelectrode, (b) applying a pulsed-D.C. current to the electrically conducting-sheet and to the counterelectrode, until catalytic metal has been deposited on the aforementioned catalytic side of the sheet (if desired, the catalytic metal, which preferably is gold, can be plated out on the fibers of the electrically-conducting sheet, so that a continuous electroplated layer of metal is formed on the surfaces of the fibers), and (c) applying a hydrophobic layer to this catalytic side or face of the electrically-conducting sheet (the opposite side of the sheet then becomes the side of the electrode to be contacted with the electrolyte of the gas-sensing cell), the thickness of this hydrophobic polymer layer being sufficient to limit gas diffusion into the cross-section of the sheet, so that the resulting electrode will operate in the current-limited mode described above.

A gas-sensing electrode made in this manner is particularly well suited for use as a cathode of a gas-sensor cell, e.g. as the oxygen cathode of a small, inexpensive, expendable oxygen-sensor cell having a useable life ranging from a few months to a year or two. This cathode has an outermost layer of hydrophobic polymer for contact with the gas stream to be analyzed but unlike a GDE, the next-to-outermost layer is the metallic (catalytic layer), and the innermost layer, for conduct with the electrotye, consists essentially of porous carbon, particularly a carbon fiber mat. It is particularly preferred that the anode of the gas-sensing cell be a metal which is more electropositive than hydrogen and is capable of being electro-oxidized in alkaline media to form alkali-soluble salts or oxides or hydroxides. Accordingly, this type of cell includes a means for bringing a stream of gas into contact with the outwardly facing the hydrophobic polymer layer. As will be apparent from the foregoing summary of the invention, oxygen-sensing cells of this invention are well suited to medical and surgical monitoring systems, e.g. systems in which the oxygen supply to a patient is monitored on a breath-by-breath basis.

Detailed Description of the Invention

Although this invention is not bound by any theory, it is presently believed that the pulsed-D.C. current treatment of the electrically conducting sheet (e.g. a fibrous carbon sheet) is a particularly important aspect of the method of preparing gas-diffusion electrodes of this invention. That is, the pulsed-D.C. electrolytic reduction of the catalytic metal ions seems to play an important role in permitting the direct deposition of adherent deposits of catalytic metal on a relatively rigid, porous, electrically-conducting sheet without loss of desired electrode performance characteristics. Pulsed direct current reduction of noble metal-containing ions is a technique which has been known for many years and has been proposed for use in the manufacture of fuel cell electrodes; see, for example, U.S. Pat. No. 3,276,976 (Juliard), issued Oct. 4, 1966. According the Juliard patent, low frequency pulsating electric current at high current density is most effective, e.g. a current density of 1 to 6 amps per square centimeter, supplied at a frequency of 30 Hz and a pulse duration of 0.2 to 5 minutes. See also U.S. Pat. No. 3,340,097 (Hess et al.), issued Sept. 5, 1967, wherein platinum/tin deposition with both pulsed and constant D.C. current is suggested (although no advantage was observed in the case of the pulsed-D.C.), the pulses being of 6.67 milliseconds duration, the current density being 15-20 mA/cm$^2$, and the pulse frequency being 30 Hz. Other non-constant currents have been suggested in this art, including cyclic voltammetry or double potential step electrolysis. See U.S. Pat. No. 4,541,905 (Kuwana), issued Sept. 17, 1985.

Because the porous, electrically-conductive sheet-like substrate on which the catalytic metal is deposited is self-supporting and has great flexural strength, it is not necessary that the hydrophobic layer in contact with the catalytic metal make any contribution whatever to the physical strength properties of the electrode. Accordingly, it is not necessary to use self-supporting fluorinated polymer films, and in this invention, the hydrophobic polymer layer can be much thinner than the porous, electrically conductive substrate, i.e. thinner than, say, 30 micrometers ($\mu$m). Indeed, the polymer layer on the "gas" side of the electrode should be just thick enough to insure that the cell will operate in a limited-current mode. By utilizing very thin polymer layers on the "gas" side, rapid gas diffusion is ensured, and response times can be kept very short. Moreover, it is not detrimental to the objectives of this invention that the porous electrically conducting sheet on which the catalytic metal is deposited is so porous and so high in void volume as to be easily flooded during cell operation. Thus, the type of electrically conducting sheet material used to make gas-diffusion electrodes of this invention can be the type of fibrous carbon sheet, obtained from woven or staple carbon fibers, which is used as a backing material for particulate phosphoric acid fuel cell electrocatalysts. Flooding of an electrode of this invention is not a problem because of the previously described need for limited current operation, in which high current densities are to be avoided rather than deliberately sought.

The following description provides additional detail regarding the various elements of an electrode of this invention and the various aspects of the methods for making and utilizing these electrodes.

The Self-Supporting Electrically-Conducting Sheet

As noted above, the physical strength properties of the self-supporting, electrically conducting sheet are of great importance in this invention, and perhaps the most important of these physical strength properties is the flexural strength (resistance to bending). (For temperature-sensitive or humidity-sensitive sheets, flexural strength can be measured at 23° C. and 50% relative humidity; in addition, flexural strength can be tested at a given L/D ratio such as 16:1; cf. ASTM Test D790.) It is also desirable that the electrically-conducting sheet have good compressive strength. Thus, rigidity is important, and flexibility is not. Sheet material having good rigidity, if balanced on a edge, will support itself, unlike a flexible film of thermoplastic polymer or a film of elastomer.

A wide variety of corrosion-resistant, fibrous or porous substrates have been utilized in electrode structures. To provide a pathway for the electrons released or taken up by the reaction occurring on the electrode surface, these substrates have low resistivity and hence are electrically conductive or semi-conductive at ordinary temperatures of cell operation, e.g. from 0 to 100 C. Metals and metalloids typically have resistivities less than $1 \times 10^{-4}$ ohm-cm at ordinary temperatures (e.g. 10°-30° C.) and are considered to be highly conductive. Solid graphite has one to two orders of magnitude greater resistivity as compared to metals and metalloids but is nevertheless an excellent conductor, as are most other economically attractive forms of carbon such as activated carbon and carbon fibers. The semiconductors have greater resistivities as compared to most forms of carbon and are typically at least one, in some cases two orders of magnitude higher in electrical resistivity. For purposes of this invention, non-conductors can be considered to have a resistivity greater than 10 ohm-cm at ordinary temperatures. True insulators have resistivities in the hundreds or thousands of ohm-cm.

The vast spectrum of resistivities (determined at ordinary temperatures such as 10°-30° C.) ranging from the metals (as low as $1 \times 10^{-6}$ ohm-cm) up to 0.1 ohm-cm or more for semiconductors includes a diverse group of materials sometimes referred to as conductive ceramics. Not all of these materials are ceramics in the strict sense of the term, but some have natural mineral analogs such as perovskite. Many of these materials are transition metal oxides and some are highly corrosion resistant as well as being electrically conductive. Typically, these compounds contain chemically combined oxygen and one or more transition metals of Groups IVB, VB, VIB, or VIII of the Periodic Table. These materials, in particulate form, can be sintered or fused to form rigid porous articles which themselves have some electrocatalytic activity and may serve as the substrate for an electocatalytic metal.

In this invention, it is generally unnecessary to resort to exotic or rare transition metal compounds to provide a substrate for electrodeposition of the catalytic metal, particularly when the electrodeposition is carried out to the point where the metal deposits plate out rather completely and adherently on a face of the electrically conductive, self-supporting sheet and preferably form a continuous or substantially continuous layer coating on the fibers or fused or sintered particles of the "catalyst" side of that sheet. Accordingly, readily available porous, sheet-like carbon materials can be used in this invention and are preferred. Some of these materials could be characterized as carbon papers or carbon cloths. They comprise woven or non-woven carbon fibers formed into a fabric, mat, or the like. The carbon fibers may be either continuous or staple and may be preimpregnated with binder resin which can, if desired be graphitized. For example, it is well known that polyacrylonitrile fibers can be bonded together with resin using air-laying or papermaking techniques, and the resulting composite can be substantially completely graphitized to form a graphite paper. These carbon papers have good electrical conductivity. (There is, however, a directional aspect to the electrical conductivity, and resistivity measured through juxtaposed fibers of the carbon paper, normalized for thickness is one to two orders of magnitude higher than resistivity measured along the longitudinal axis of a fiber; carbon papers utilized in this invention have a resistivity less than 0.5 ohm-cm measured in any direction and less than 0.1 ohm-cm measured parallel to fiber lengths.) Carbon papers made by papermaking techniques from chopped carbon fiber tend to have higher electrical resistivity than those made by a molding method using milled carbon fiber. However, resistivity values can be lowered by selecting a suitable binder resin and optimizing the preimpregnation and graphitization conditions. In this manner, the electrical resistivity through juxtaposed fibers of the carbon paper can be lowered to less than 0.1 ohm-cm, and the resistivity parallel to the longitudinal axis of a fiber in the plane of the paper can be lowered to less than 0.01 ohm-cm.

Carbon paper thicknesses can range all the way from a few micrometers to as much as a millimeter or two. Uniformity of thickness is desirable. In the context of the present invention, carbon papers may have thicknesses in excess of 50 micrometers ($\mu$m) to insure good rigidity, but thicknesses in excess of 500 $\mu$m are generally unnecessary and may even detract from response time. Accordingly, it is particularly preferred that carbon papers utilized as self-supporting, electrically conductive substrates for electrocatalytic metals range in thickness from about 100 to 400 $\mu$m (about 0.1 to about 0.4 mm).

It is essential that the electrically conductive sheet material be porous, so that gases and other fluids (e.g. gases and electrolytes) can penetrate into the electrode structure. (However, it is not essential that the electrically conductive sheet material be hydrophilic, because wetting techniques can be used to obtain electrolyte penetration.) Void volumes can be as large as 50% or higher, e.g. 50–95%, the optimum void volume being roughly 60–90%. Because of the high void volume, the bulk density or apparent density is far less than the density of graphite (2.3 g/cm$^2$). Typical bulk densities for porous carbon sheets are greater than 0.2 g/cm$^2$ but less than 1.0 g/cm$^2$, e.g. 0.3–0.6 g/cm$^2$. Because of the high void volume, and because the voids interconnect and provide pathways through the sheet material, gas permeability of most carbon papers is high. Moreover, the pores in these paper-like structures are relatively large, e.g. well in excess of 10 μm and may even approach 100 μm. Gas permeability values expressed as 1/cm$^2$·hr·mmaq, i.e. cm$^{-2}$·hr$^{-1}$·mmaq$^{-1}$, tend to be dependent upon the thickness of the sheet material. When the thickness of the carbon paper is greater than one millimeter, the gas permeability can be as low as 1.0 cm$^{-2}$·hr$^{-1}$·mmaq$^{-1}$ (e.g about 0.5, same units), but as the thickness decreases to 100 μm or less, gas permeability can increase to as much as 40 or 50 (same units). Gas permeability values greater than 5.0 or even 1.0 or 2.0 (same units) are not essential to this invention, however, and outstanding results have been obtained with relatively thick carbon papers (thicker than 300 μm) having a gas permeability less than 5.0 (same units).

Deviations from uniformity of thickness in carbon paper materials can also vary somewhat with thickness, the thicker materials exhibiting greater thickness deviations from the average thickness value. In any event, thickness deviations can be controlled to within ±40 μm, e.g. ±10–40 μm.

Corrosion currents measured with commercially available carbon papers useful in this invention can be small, e.g. after 100 minutes in concentrated phosphoric acid (which can be superconcentrated, i.e. P$_2$O$_5$-containing phosphoric acid) at 190° C. and a voltage of 0.8v vs. RHE, these currents are less than one microampere per milligram of paper substrate.

As noted previously, one of the most important properties of the carbon paper is its high rigidity. This rigidity is much like that of heavy construction paper. The flexural strength of commercially available carbon papers used as backing material for gas-diffusion electrodes in fuel cells is very high. Flexural strength values in excess of 2000 kPa are easily obtained. The preferred, commercially available graphite papers used in this invention can have a flexural strength in excess of 15000 kPa, e.g. 2500 p.s.i. (about 17500 kPa). These rigid graphite papers are available from Toray Industries, Inc., Carbon Fibers Department, Tokyo, Japan. These graphite papers contain "TORAYCA" (trade designation) carbon fiber, which is obtained from polyacrylonitrile. Although carbon papers made from "TORAYCA" carbon fiber have been developed for applications ranging from aerospace products to sporting goods, the "TGP" (trade designation) Toray Graphite papers have been developed specifically for the electrode substrate of a supported electrocatalyst used in phosphoric acid fuel cells. (In a typical practice in the fuel cell art, a supported catalyst such as platinum on carbon black is combined with hydrophobic polymer particles and is formed into a layer on the "TGP" substrate.) The "TGP" graphite papers have high tensile strength and high modulus. Porosities of these papers range from 70 to 82%, thicknesses range from 0.1 to 0.37 mm, and bulk densities range from 0.35 to about 0.5 g/cm$^3$ Electrical resistivity in the plane of the paper is less than 0.01 ohm-cm.

THE CATALYTIC METAL

As is well known in the art of electrochemistry generally and in the art of electrodes in particular, several transition metals have atomic structures which facilitate the electrooxidation and/or electroreduction of gases such as oxygen, oxides of carbon and sulfur and nitrogen, halogens, volatile organic compounds, etc. Typically, the most effective catalytic metals are found in Groups IB, VIII, and VIB or VIIB of the Periodic Table, and of these, the Group IB metals and the metals of the second and third triads of Group VIII are particularly preferred. In the present invention, the most conveniently manufactured gas-sensing cells are alkaline, particularly the alkaline metal/oxygen cells which are effective as oxygen-sensing devices. Accordingly, gas-sensing electrodes made according to this invention are typically oxygen cathodes for alkaline cells and preferably contain a catalytic metal which is stable and resistant to corrosion in alkaline media. Of all of the transition metals discussed previously, gold and gold alloys are considered to be the most stable and alkaline resistant in these alkaline cells. The catalytic metal can, therefore, be 100% gold or an alloy containing a major amount of gold, preferably at least 80 atomic percent of gold. Silver, platinum, palladium, nickel, and electrically conductive transition metal oxides are less preferred. The gold can be electrodeposited on the face of a self-supporting sheet (such as one of the carbon papers described previously) to the extent that the gold forms a continuous metallic layer on the surfaces of the fibers (or, as the case may be, on the surfaces of fused or sintered particles or other porous, self-supporting sheet structures), and as a result, there are no significant gaps or pores in the metallic layer except as necessitated by the structure of the self-supporting sheet itself. Typically, the naked eye perceives a thin, paper-like substrate covered by bright, electroplated metal, much like any metal plating on a smoother substrate such as plastic or metal sheeting.

THE HYDROPHOBIC POLYMER LAYER

An important feature of an electrode of this invention is the thin polymer barrier which limits the access of gas to the face coated with the catalytic metal; in other words, this polymer layer serves as a gas diffusion barrier slowing down the rate of diffusion of gas into the electrode structure. For fast response times, the polymer layer should be very thin, but still thick enough to limit the current produced by the cell. Current densities below 10 mA/cm$^2$ and even below 5 mA/cm$^2$ (e.g. in the microampere range) are, thus, insured by the presence of the polymer layer.

Unlike a typical fuel cell GDE structure, a gas-sensing electrode of this invention is provided with a continuous or substantially continuous, relatively non-porous hydrophobic polymer layer on the outermost ("gas") side of the electrode. Typically, there are essentially no inorganic particles dispersed in the hydrophobic layer, so that this layer can present a significant diffusion barrier to the oncoming gas stream. Moreover, because of the relatively low porosity of the polymer layer, this layer becomes easily saturated with the gas, and the thus-trapped gas is easily flushed from the layer by additional incoming gas.

The selection of a suitable hydrophobic polymer is governed by factors well known in this art. Typically, the polymer is made from an unsaturated halogenated monomer, at least some of the halogen atoms being fluorine (although some can be chlorine atoms). The preferred fluorinated polymer is polytetrafluoroethylene (PTFE), commercially available as various types of "TEFLON" (trademark). Other useful hydrophobic polymers include poly(trifluorochloroethylene), polyvinylidene fluoride, poly(hexafluoropropene), and the like, including co-polymers of these various halogenated unsaturated monomers and various mixtures and combinations of these hydrophobic polymers. The polyfluorocarbons appear to be the most inert of these polymers.

COUNTERELECTRODES

Since the preferred electrodes of this invention are cathodes, the preferred counterelectrode for a gas-sensing cell is an anode. (The counter-electrode used in the method of this invention is also an anode but serves a different purpose.) The anode may be electrocatalytically active or may be inert (merely providing electrical contact with the electrolyte) but is preferably comprised of an active metal more electropositive than hydrogen. Stated another way, the half-cell $E_o$ for the oxidation of the metal is preferably a value greater than 0.0, e.g. at least +0.1. Suitable metals include lead ($Pb/Pb^{+2}$ $E^0 = +0.126$), cadmium ($Cd/Cd^{+2}$ $E^0 = +0.4$), zinc ($Zn/Zn^{+2}$ $E^0 = +0.76$), and the like. (The half-cell $E^o$ for the corresponding reductions of metal ion to metal would be $-0.126$, $-0.4$, $-0.76$, etc.). It is preferred to avoid selecting metals which oxidize in alkaline media to form alkali-insoluble metal oxides, since the relative ratio of metal to metal oxide may then have an effect upon the electrode potential, thereby making it difficult to maintain a constant voltage for the cell. In the case of lead, zinc, cadmium, and the like, the oxides and hydroxides of these metals dissolve in typical alkaline media and thus are helpful in providing a cell with a constant-potential electricity output. (The reliability and steadiness of the electricity output for a given gas concentration is far more important than the magnitude of the electricity output.) Lead anodes are well suited for use in oxygen-sensing cells of this invention and are normally preferred in view of the low cost and ready availability of metallic lead. The lead can be in the form of a powder which is packed or compressed into a particularly desired shape. The supply of lead in the cell is normally large enough so that the cell can continue to produce electricity for months or even years as a metal/oxygen primary cell. The primary limiting factor on cell life does not appear to be the rate of consumption of the metallic anode, but rather the tendency of dissolved anode metal to plate out on the cathode, thereby interfering with cathode performance. Despite this tendency to plate out metal on electrolyte side of the cathode, a cell life in excess of six months is easily achieved with this invention. Although this invention is not bound by any theory, it is believed that the dissolved metal plates out on the self-supporting electrically conducting sheet (e.g. on carbon fibers in the sheet) before it can reach the catalytic layer and poison the catalyst, thereby extending the life of the cell.

In the method of this invention, wherein pulsed-D.C. is applied to a cell to obtain electrodeposition of catalytic metal on the self-supporting electrically conducting sheet, the principal function of the anode is merely to provide electrical contact with the electrolyte.

ELECTROLYTES

As noted previously, alkaline electrolytes are preferred and can be aqueous solutions of alkali metal hydroxides (NaOH, KOH, LiOH, or, less preferably, CsOH), or other hydroxides. Alkali metal carbonates can be used if the selection of carbonates is optimized for electrical conductivity (low internal cell resistance). Adequate solid alkaline electrolytes are presently not available but are not, in theory, precluded.

If the electrolyte is acidic, it may be either liquid or solid. Preferred liquid acidic electrolytes include aqueous solutions of common mineral acids such as sulfuric, phosphoric, hydrohalic (e.g. HCl), and perchloric acids. Preferred solid electrolytes comprise fluorinated polymers containing sulonic acid groups. Theoretically, the electrolyte does not need to be a strong acid or a strong base, but neutral (e.g. salt-containing) electrolytes are less preferred.

As used herein, the term "electrolyte" should be understood to include both a single electrolyte and anolyte/catholyte combinations, i.e. electrolytes divided by anionic or cationic exchange membranes. As is known in the art, it is not essential that the "electrolyte" in contact with the cathode be exactly the same substance that is in contact with the anode. In divided electrolytes, a complete ionic pathway is provided from cathode to anode, just as in single electrolyte cells. In other words, "electrical contact" merely requires an ion pathway, not physical contact. In preferred embodiments of this invention, there is no advantage to be gained by dividing the electrolyte, however.

For oxygen-sensing devices adapted specifically for medical and surgical uses, the physical size of the cell may be relatively small, hence the internal volume of the cell can be less than 50 or 100 ml, more typically less than 5 or 10 ml. At least about 0.1 ml of the electrolyte will normally be needed.

EXTERNAL CIRCUIT AND GALVANOMETRIC MEASURING MEANS

As is well known in the art, the Cathode and anode of a cell can be provided with suitable leads, so that an electrical pathway can be provided between the electrodes external to the electrolyte of the cell.

The external circuit can include resistors, switches, and various other electrical components as well as galvanometric measuring devices such as voltmeters or ammeters. As is commonly done in this art, it is preferred to correlate the content of gas component to be measured to an amperometric measurement, such that essentially zero current is observed when the gas component (e.g. oxygen) is completely absent, and maximum cell output (which may be in the microamperes per square centimeter of electrode surface) when the gas stream fed to the sensing electrode consists of 100% of the aforementioned gas component. In the amperometric approach, it is preferred that the cell potential remain substantially constant.

For effective cell operation, of course, the sensing electrode is provided with a means for channelling the gas stream over, agains, or into the "gas" side of the electrode.

METHOD OF PREPARATION OF ELECTRODES

As will be apparent from the foregoing description, two of the most important steps in the preparation of aan electrode of this invention are the pulsed-current electrodeposition step and the application of the hydrophobic polymer to the face on which the electrodeposition took place. The gold or other catalytic metal is electrodeposited from a gold plating bath solution using a rectangular pulse current waveform with an average current density of about 1 to 50mA/cm$^2$, a pulse duty cycle of 1 to 50%, a peak current density which is typically less than 5.0 A/cm$^2$, and a pulse frequency of 1 to 100 Hz, e.g. 5–30 Hz. The particular pulse current wave form should be selected so as to favor the plating effect and to favor adherent coating on the surface of the electrically conduction sheet. Accordingly, the peak current is preferably greater than 50 mA/cm$^2$, and the pulse on-time is preferably shorter than one second, the pulse duty cycle being preferably in the range of 5 to 20%. The operating temperature is preferably within normal room temperature limits (20°–25° C.). The gold plating solution can contain any of the conventional gold salts or gold (I) or gold (III)-containing ions, e.g. gold cyanide, gold chloride, (preferably AuCl$_3$), AuCl$_4$, and the like.

The pulsed-current electrodeposition results in an electrode with uniform coverage of gold (or other catalytic metal) on the surface of the carbon paper. The electrodeposited metal layer has excellent adherence to the carbon paper, and catalytic metal loadings less than 5 mg/cm$^2$ have been found to be effective, e.g. 0.5–2 mg/cm$^2$.

Pulsed-current deposition provides enhanced deposits as compared to constant DC electrodeposition. That is, the pulsed-current deposits are more uniform and adherent. The uniform coating of individual carbon fibers seems to be obtained only with the pulsed-current technique. These findings are surprising in that very little is known concerning the direct deposit of catalytic metals on porous carbon papers with high flexural strength. As noted previously, these carbon papers are most typically used as a backing material for supported platinum catalysts and the like.

The application of the hydrophobic polymer layer to the catyltic side of the electrode can be carried out in a conventional manner, provided the coating is thick enough to provide a gas diffusion barrier while at the same time being thin enough to permit rapid response times. Suspensions and dispersions of hydrophobic polymers are readily available, and the resulting polymer coating can be sintered to a continuous film at relatively modest temperatures. Alternatively, a very thin film of polymer (much thinner than the electrically conductive sheet material) can be pre-formed and laminated to the "gas" side of the electrically conductive sheet material.

The following Examples illustrate the principle and practice of this invention.

EXAMPLE

Rigid gold electrodes were prepared on carbon paper support material. The carbon paper material was Toray "TGP 30" for some of the electrodes, and "TGP 120" for others. As noted above, "TGP" (Toray Graphite Paper) is a trade designation of Toray Industries, Inc. of Tokyo, Japan for materials which have been developed specifically for backing the supported noble metal catalyst of gas diffusion electrodes used in phosphoric acid fuel cells. The properties of "TGP 30" and "TGP 120" are set forth below.

| PROPERTIES OF TORAY GRAPHITE PAPERS | | |
|---|---|---|
| | TGP 30 | TGP 120 |
| average thickness, mm | 0.10 | 0.37 |
| bulk density, g/cm$^3$ | 0.35–0.44 | 0.41–0.49 |
| porosity, % | 72–82 | 70–80 |
| gas permeability, cm.$^{-2}$hr.$^{-1}$mmaq$^{-1}$ | 15–30 | 2 |
| electrical resistivity: | | |
| Through plane, ohm-cm | <0.15 | <0.15 |
| in plane, ohm-cm | <0.01 | <0.01 |
| pore size, measured by mercury porosimeter | — | <10% <20 μm <90% in range of 20–60 μm |
| surface smoothness variations, μm | approx. ±25 | approx. ±25 |
| flexural strength, p.s.i. | 2.5 × 10$^3$ | 2.5 × 10$^3$ |

The gold was electrodeposited from a cyanide gold plating bath solution (obtained from Technics, Inc.). The selective electrodeposition of gold was carried out using a rectangular pulse current waveform with an average current density of 10 mA/cm$^2$, a pulse duty cycle of 10%, a peak current density of 100 mA/cm$^2$, and a pulse frequency of 10 Hz. The operating temperature was 23° C. The highly adherent gold coatings thus obtained exhibited an average gold loading of 1.6 mg/cm$^2$, determined gravimetrically.

The gold-coated TGP (Toray Graphite Paper) was laminated to a PTFE film, the PTFE film being applied to the gold-coated face of the Toray paper. Four electrodes were prepared with overall areas of 110 square inches each. These electrodes could be die-cut to form small circles, each having an area of 2.5 to 3.0 square centimeters.

The resulting gold-containing gas-diffusion electrodes were assembled into oxygen gas analyzing cells and evaluated for oxygen-sensing performance. The evaluation included: (1) baseline cell output in the absence of oxygen, (2) output response in pure oxygen and pure air, (3) linearity of the cell output over the 0 to 100% range of oxygen concentration, and (4) the response time in switching from air to pure oxygen. The results of the testing of the first of 8 sample electrodes are tabulated and presented below:

| % O$_2$ IN GAS STREAM vs. CELL POTENTIAL | | |
|---|---|---|
| A. | Output response, i.e. cell potential, measured when simulated pure air (20% O$_2$, 80% N$_2$) is fed to the cathode, 5 minute response time (mV) | 13.14 |
| B. | Theoretical 100% O$_2$ output response (5 × 13.14 mV): | 65.70 |
| C. | Actual output response (potential) measured after changing cathode feed gas from simulated air to 100% O$_2$ | |
| | C-15: 15 second response time, mV: | 63.085 |
| | compared to B, (65.70 mV), %: | 96.02 |
| | C-30: 30 second response time, mV: | 64.53 |
| | compared to B (65.70 mV), %: | 98.22 |
| | C-45: 45 second response time, mV: | 64.92 |
| | compared to B (65.70 mV), %: | 98.81 |
| | C-60: 60 second response time, mV: | 65.18 |
| | compared to B (65.70 mV), %: | 99.21 |
| | C-300: 5 minute response time, mV: | 66.31 |
| | compared to B (65.70 mV), %: | 100.93 |
| | C-600: 10 minute response time, mV: | 66.28 |
| | compared to B (65.70 mV), %: | 100.88 |
| D. | Re-establishing simulated air feed | 13.17 |

-continued

% O₂ IN GAS STREAM vs. CELL POTENTIAL

| | | |
|---|---|---|
| | and rereading cell potential, 5 minute response time (mV) | |
| E. | Re-establishing 100% O₂ feed and rereading cell potential, 5 minute response time (mV): | 66.31 |
| | compared to B (65.70 mV), %: | 100.93 |
| F. | Actual output (potential) for 0% O₂ (100% N₂), five minute response time, (mV): | 0.10 |

The foregoing data indicate a reliable, responsive oxygen-sensing cell capable of providing accurate analytical readings, because the curve for the relationship % O₂ vs. cell potential is almost exactly linear (in view of readings taken at 0%, 20% and 100% O₂).

The data for the other seven sample electrodes is tabulated below. The meanings of the column headings (A through F) of this Table have been defined above.

TABLE*

| | A | C | % of 5 × A | | | | | D | E | F |
|---|---|---|---|---|---|---|---|---|---|---|
| Sample No. | (mV) | C-15 | C-30 | C-45 | C-60 | C-300 | C-600 | (mV) | (mV) | (mV) |
| 2 | 13.50 | 93.43 | 94.68 | 98.79 | 99.24 | 101.13 | 100.92 | 13.67 | 101.15 | 0.13 |
| 3 | 14.66 | 95.74 | 98.24 | 98.94 | 99.29 | 101.06 | 101.12 | 14.76 | 101.06 | 0.12 |
| 4 | 12.05 | 96.14 | 98.28 | 98.96 | 99.37 | 100.20 | 100.38 | 12.16 | 100.38 | 0.12 |
| 5 | 12.49 | 93.36 | 95.22 | 97.02 | 98.15 | 101.04 | 101.11 | 12.60 | 101.12 | 0.09 |
| 6 | 16.01 | 95.47 | 98.06 | 98.77 | 99.18 | 100.52 | 100.46 | 16.07 | 100.39 | 0.14 |
| 7 | 16.12 | 93.82 | 97.52 | 98.52 | 99.02 | 100.49 | 100.46 | 16.20 | 100.42 | 0.10 |
| 8 | 13.31 | 95.23 | 98.26 | 99.01 | 99.36 | 100.67 | 100.64 | 13.35 | 100.64 | 0.07 |

*Brief summary of definitions of column headings:
A: Output response, 20% O₂, 5 min.
C: Output response in % of 5 × A after switching to 100% O₂
C-15: % after 15 sec.
C-30: % after 30 sec.
C-45: % after 45 sec.
C-60: % after 60 sec.
C-300: % after 5 min.
C-600: % after 10 min.
D. Re-read of A
E. Re-read of C-300
F. Output response, 0% O₂, 5 min.

Although the preferred embodiments of this invention have been described in particular detail with respect to oxygen-sensing electrodes, other gases can be detected or analyzed in accordance with the principles of this invention, including hydrogen, organic compounds, SO₂, NO, H₂S, etc. as well as hazardous gases used in manufacturing, including toxic or highly reactive hydrides such as phosphine, arsine, silane, borane, and the like.

What is claimed is:

1. A method for making a sheet-shaped, current-limited, catalytic, gas-sensing electrode having a flexural strength of at least about 2000 kilopascals, comprising the steps of:
   (a) bringing an exposed face of a self-supporting, electrically conducting sheet having a thickness of at least about 30 micrometers and a flexural strength of at least 2000 kilopascals into contact with an electrolyte containing ions of a catalytic metal, said electrolyte being in electrical contact with a counterelectrode,
   (b) applying a pulsed-D.C. current to said self-supporting sheet and said counterelectrode, until catalytic metal has been deposited on said exposed face of said electrically-conducting sheet, thereby providing a catalytic metal-coated self-supporting electrically conducting sheet,
   (c) applying to the thus-coated face of the catalytic metal-coated self-supporting electrically conducting sheet a hydrophobic polymer layer which is thick enough to limit reducible or oxidizable gas diffusion into said catalytic metal-coated self-supporting electrically-conducting sheet such that, when the catalytic metal-coated self-supporting electrically conducting sheet with the applied hydrophobic layer is utilized as a catalytic, gas-sensing electrode in a primary or secondary current-generating cell to generate current, density of said current cannot exceed 20 mA/cm².

2. A method according to claim 1, wherein:
   (a) said self-supporting, electrically conducting sheet comprises carbon fibers, has a thickness ranging from about 50 to about 500 micrometers, and has a flexural strength greater than 5000 kilopascals;
   (b) said pulsed-D.C. current is pulsed at a rate of about 1 to about 100 Hz; the ions of catalytic metal are ions containing gold, and
   (c) said hydrophobic polymer layer is thick enough to limit the current producible by the catalytic metal-coated self-supporting electrically-conducting sheet to less than 10 mA/cm².

3. A sheet-shaped, current-limited, catalytic, gas-sensing electrode having a flexural strength of at least about 2000 kilopascals made by the method of claim 1.

4. A gas-sensing electrochemical cell comprising an anode, a cathode, an electrolyte in electrical contact with said anode and cathode, and an external electrical circuit means connecting said cathode and anode, wherein the cathode is the sheet-shaped current-limited, catalytic, gas-sensing electrode of claim 3.

5. A gas-sensing electrochemical cell according to claim 4, wherein the hydrophobic polymer layer is thick enough to limit the current producible by the catalytic metal-coated self-supporting electrically conducting sheet to less than 10 mA/cm².

6. A gas-sensing electrochemical cell according to claim 4, wherein the electrolyte of said cell is alkaline, said cathode comprises a catalytic metal-coated, self-supporting fibrous carbon sheet, and the metal in the metal coating on the self-supporting fibrous sheet consists essentially of metallic gold in an amount of from 0.1 to 5 mg per geometric square centimeter of said fibrous carbon sheet.

7. A gas-sensing electrochemical cell according to claim 4, wherein said electrochemical cell includes means for bringing a gas stream containing oxygen into contact with a face of the cathode of said cell, said electrochemical cell being constructed and arranged to sense the oxygen in the stream and to measure amounts of the oxygen in the stream, thereby determining the concentration of oxygen in the stream.

8. A gas-sensing electrochemical cell according to claim 7, wherein the external electrical circuit means of said cell includes a galvanometric measurement means, for measuring changes in electrochemical cell performance, and wherein changes in electrochemical cell performance measured by said galvanometric measurement means are calibrated to correspond to the content of oxygen in said gas stream.

9. A gas-sensing electrochemical cell according to claim 7, wherein the hydrophobic polymer layer on the catalytic metal-coated, self-supporting electrically-conducting sheet is thin enough to permit the electrochemical cell to respond to and measure a change in said concentration of the oxygen in the gas stream in less than 5 seconds.

10. A gas-sensing electrochemical cell according to claim 9, wherein the hydrophobic polymer layer on said sheet is thin enough to permit the electrochemical cell to respond to and measure a change in the concentration of the oxygen in the gas stream in less than one second.

11. A gas-sensing electrochemical cell according to claim 7, wherein the anode comprises an electrochemically oxidizable metal.

12. A method for measuring the content of a gaseous component of a gas stream, which comprises the step of bringing a gas stream into contact with the gas-sensing electrode of a cell comprising said gas-sensing electrode, an electrolyte in electrical contact with the gas-sensing electrode and a counterelectrode, and an electrical circuit means electrically connecting the gas-sensing electrode to the counterelectrode, wherein said gas-sensing electrode is the electrode of claim 3.

13. A gas-sensing electrode according to claim 3, wherein said self-supporting, electrically conducting sheet has a void volume of at least 50%.

14. A gas-sensing electrode according to claim 13, wherein said void volume is about 60-90%.

15. A gas-sensing electrochemical device comprising a metallic anode, a cathode, an alkaline electrolyte in electrical contact with the anode and the cathode, an electrical circuit means for electrically connecting the anode to the cathode, a galvanometric measuring means sensitive to cell performance connected to said electrical circuit means, and means for bringing a gas stream containing a reducible gas into contact with the cathode, wherein said cathode comprises:
   (a) a self-supporting porous, electrically-conductive fibrous carbon sheet 50 to 500 micrometers in thickness having a flexural strength greater than 5000 kilopascals,
   (b) electrodeposited by pulsed direct current on the carbon fibers of a first face of said sheet, 0.1 to 5 mg, per geometric square centimeter of said first face, of a metal consisting essentially of gold, a face opposite said first face being in contact with said alkaline electrolyte of the gas-sensing electrochemical device, and
   (c) laminated to said first face of said sheet, a hydrophobic polymer layer thick enough to keep any current density output of the cell below 5 milliamps per square centimeter of electrode face but thin enough to permit the device to respond to and measure a change in concentration of said reducible gas within about one second,
   said means for bringing a gas stream containing a reducible gas into contact with the cathode being constructed and arranged to bring said gas stream into contact with the thus-laminated hydrophobic polymer layer.

16. A gas-sensing electrochemical device according to claim 15, wherein the metallic anode consists essentially of an electrochemically oxidizable metal more electropositive than hydrogen, and wherein the reducible gas is oxygen.

17. A gas-sensing electrochemical device according to claim 15, wherein said self-supporting porous, electrically-conductive fibrous sheet has a void volume of at least 50%.

18. A gas-sensing electrochemical device according to claim 17, wherein said void volume is about 60-90%.

* * * * *